United States Patent
Wollenberg

(10) Patent No.: US 8,249,816 B2
(45) Date of Patent: Aug. 21, 2012

(54) HIGH THROUGHPUT SCREENING METHODS FOR FUEL COMPOSITIONS

(75) Inventor: Robert H. Wollenberg, Orinda, CA (US)

(73) Assignee: Chevron Oronite Company, LLC, San Ramon, CA (US)

( * ) Notice: Subject to any disclaimer, the term of this patent is extended or adjusted under 35 U.S.C. 154(b) by 1659 days.

(21) Appl. No.: 10/779,419

(22) Filed: Feb. 13, 2004

(65) Prior Publication Data

US 2005/0182572 A1  Aug. 18, 2005

(51) Int. Cl.
  *G01N 31/00*  (2006.01)
(52) U.S. Cl. .......................... 702/22; 436/139
(58) Field of Classification Search ...... 73/53.01–61.79; 436/139; 702/22
  See application file for complete search history.

(56) References Cited

U.S. PATENT DOCUMENTS

| | | | |
|---|---|---|---|
| 5,306,315 A * | 4/1994 | Cherpeck | 44/424 |
| 5,399,178 A * | 3/1995 | Cherpeck | 44/415 |
| 5,814,110 A * | 9/1998 | Bartz et al. | 44/370 |
| 5,959,297 A | 9/1999 | Weinberg et al. | |
| 5,985,356 A | 11/1999 | Schultz et al. | |
| 6,004,617 A | 12/1999 | Schultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,296,771 B1 | 10/2001 | Miroslav | |
| 6,326,090 B1 | 12/2001 | Schultz et al. | |
| 6,336,353 B2 | 1/2002 | Matsiev et al. | |
| 6,345,528 B2 | 2/2002 | Petro et al. | |
| 6,346,290 B1 | 2/2002 | Schultz et al. | |
| 6,371,640 B1 | 4/2002 | Hajduk et al. | |
| 6,373,570 B1 | 4/2002 | McFarland et al. | |
| 6,393,895 B1 | 5/2002 | Matsiev et al. | |
| 6,393,898 B1 | 5/2002 | Hajduk et al. | |

(Continued)

FOREIGN PATENT DOCUMENTS

EP  0658573  6/1995

(Continued)

OTHER PUBLICATIONS

Heneghan et al., Journal of Engineering for Gas Turbines and Power—Transactions of the ASME, (Jul. 1993) vol. 115, No. 3, pp. 480-485.*

(Continued)

*Primary Examiner* — Hezron E Williams
*Assistant Examiner* — Hoang Nguyen

(57) ABSTRACT

Methods for determining deposit formation tendencies for a plurality of fluid samples of different compositions is provided. Each sample includes fuel additive compositions containing one or more fuel additives or fuel compositions containing one or more fuels and one or more fuel additives. The methods can advantageously be optimized using combinatorial chemistry, in which a database of combinations of fuel compositions are generated. As market conditions vary and/or product requirements or customer specifications change, conditions suitable for forming desired products can be identified with little or no downtime.

19 Claims, 2 Drawing Sheets

U.S. PATENT DOCUMENTS

| | | | |
|---|---|---|---|
| 6,395,552 B1 | 5/2002 | Borade et al. | |
| 6,401,519 B1 | 6/2002 | McFarland et al. | |
| 6,406,632 B1 | 6/2002 | Safir et al. | |
| 6,410,331 B1 | 6/2002 | Schultz et al. | |
| 6,419,881 B1 | 7/2002 | Weinberg et al. | |
| 6,420,179 B1 | 7/2002 | Schultz et al. | |
| 6,436,292 B1 | 8/2002 | Petro | |
| 6,438,497 B1 | 8/2002 | Mansky et al. | |
| 6,440,745 B1 | 8/2002 | Weinberg et al. | |
| 6,441,901 B2 | 8/2002 | McFarland et al. | |
| 6,461,515 B1 | 10/2002 | Safir et al. | |
| 6,468,806 B1 | 10/2002 | McFarland et al. | |
| 6,475,391 B2 | 11/2002 | Safir et al. | |
| 6,484,567 B1 | 11/2002 | Hajduk et al. | |
| 6,491,816 B2 | 12/2002 | Petro | |
| 6,508,984 B1 | 1/2003 | Turner et al. | |
| 6,519,032 B1 | 2/2003 | Kuebler et al. | |
| 6,528,026 B2 | 3/2003 | Hajduk et al. | |
| 6,535,284 B1 | 3/2003 | Hajduk et al. | |
| 6,535,824 B1 | 3/2003 | Mansky et al. | |
| 6,536,944 B1 | 3/2003 | Archibald et al. | |
| 6,541,271 B1 | 4/2003 | McFarland et al. | |
| 6,553,318 B2 | 4/2003 | Mansky | |
| 6,576,906 B1 | 6/2003 | Archibald et al. | |
| 6,577,392 B1 | 6/2003 | Nielsen et al. | |
| 6,582,116 B2 | 6/2003 | Nielsen | |
| 6,605,473 B1 | 8/2003 | Hajduk et al. | |
| 6,644,101 B2 | 11/2003 | Hajduk et al. | |
| 6,649,413 B1 | 11/2003 | Schultz et al. | |
| 6,650,102 B2 | 11/2003 | Hajduk et al. | |
| 6,653,138 B1 | 11/2003 | Turner et al. | |
| 6,655,194 B2 | 12/2003 | Hajduk et al. | |
| 6,658,429 B2 | 12/2003 | Dorsett, Jr. | |
| 6,664,067 B1 | 12/2003 | Hajduk et al. | |
| 6,668,622 B2 | 12/2003 | Hajduk et al. | |
| 6,670,298 B1 | 12/2003 | Weinberg et al. | |
| 6,679,130 B2 | 1/2004 | Hajduk et al. | |
| 6,681,618 B2 | 1/2004 | Hajduk et al. | |
| 6,686,205 B1 | 2/2004 | Schultz et al. | |
| 6,690,179 B2 | 2/2004 | Mansky et al. | |
| 6,713,264 B2 * | 3/2004 | Luttermann et al. | 435/7.1 |
| 2002/0023507 A1 | 2/2002 | Hajduk et al. | |
| 2002/0028456 A1 | 3/2002 | Mansky et al. | |
| 2002/0029621 A1 | 3/2002 | Hajduk et al. | |
| 2002/0032531 A1 | 3/2002 | Mansky et al. | |
| 2002/0090320 A1 * | 7/2002 | Burow et al. | 422/64 |
| 2002/0098332 A1 | 7/2002 | Warren et al. | |
| 2002/0148282 A1 | 10/2002 | Hajduk et al. | |
| 2002/0155036 A1 | 10/2002 | Hajduk et al. | |
| 2002/0164275 A1 | 11/2002 | Wheeler et al. | |
| 2003/0007152 A1 | 1/2003 | McFarland et al. | |
| 2003/0032198 A1 | 2/2003 | Lugmair et al. | |
| 2003/0032205 A1 | 2/2003 | McFarland et al. | |
| 2003/0037601 A1 | 2/2003 | Mansky et al. | |
| 2003/0037620 A1 | 2/2003 | Mansky | |
| 2003/0041653 A1 | 3/2003 | Matsiev et al. | |
| 2003/0041671 A1 | 3/2003 | Hajduk et al. | |
| 2003/0041672 A1 | 3/2003 | Hajduk et al. | |
| 2003/0041676 A1 | 3/2003 | Hajduk et al. | |
| 2003/0054740 A1 | 3/2003 | Mansky | |
| 2003/0055587 A1 | 3/2003 | Wang et al. | |
| 2003/0056576 A1 | 3/2003 | Mansky | |
| 2003/0068829 A1 | 4/2003 | Giaquinta et al. | |
| 2003/0097871 A1 | 5/2003 | Mansky | |
| 2003/0100119 A1 | 5/2003 | Weinberg et al. | |
| 2003/0127776 A1 | 7/2003 | Carlson et al. | |
| 2003/0133113 A1 | 7/2003 | Hajduk et al. | |
| 2003/0138025 A1 | 7/2003 | Archibald et al. | |
| 2003/0141613 A1 | 7/2003 | Hajduk et al. | |
| 2003/0142309 A1 | 7/2003 | Kuebler et al. | |
| 2003/0157721 A1 | 8/2003 | Turner et al. | |
| 2003/0161763 A1 | 8/2003 | Erden et al. | |
| 2003/0169638 A1 | 9/2003 | Nielsen | |
| 2003/0171226 A1 | 9/2003 | Gatto | |
| 2003/0190260 A1 | 10/2003 | Wheeler et al. | |
| 2003/0203500 A1 | 10/2003 | Carlson et al. | |
| 2003/0211016 A1 | 11/2003 | Dales et al. | |
| 2003/0218467 A1 | 11/2003 | Carlson et al. | |
| 2003/0219906 A1 | 11/2003 | Giaquinta et al. | |
| 2004/0123650 A1 | 7/2004 | Kolosov et al. | |
| 2004/0230397 A1 * | 11/2004 | Chadwick | 702/181 |

FOREIGN PATENT DOCUMENTS

| | | |
|---|---|---|
| WO | WO 02/07870 | 1/2002 |

OTHER PUBLICATIONS

Heneghan et al., Journal of Engineering for Gas Turbines and Power-Transactions of the ASME, (Jul. 1993) vol. 115, No. 3, pp. 480-485).*

Heneghan et al., Journal of Engineering for Gas Turbines and Power Transaction of the ASME, (Jul. 1993) vol. 155(3):480-485.*

International Search Report issued in European Patent Application No. 05713294.6.

* cited by examiner

HIGH THROUGHPUT SCREENING METHODS FOR FUEL COMPOSITIONS

BACKGROUND OF THE INVENTION

1. Technical Field

The present invention relates generally to methods for high throughput screening of fuel compositions.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the fuel industry involves individually forming candidate fuel compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading compositions.

However, present research in the fuel industry does not allow for reformulation to occur in an expeditious manner. As such, there exists a need in the art for a more efficient, economical and systematic approach for the preparation of fuel compositions and screening of such compositions. For example, fuel compositions have deposit forming tendencies from, for example, the combustion of fuel in an internal combustion engine. This will result in the formation and accumulation of deposits on various parts of the combustion chamber and on the fuel intake and exhaust systems of the engine. The presence of these deposits in the combustion chamber often result in the following problems: (1) reduction in the operating efficiency of the engine; (2) inhibition in the heat transfer between the combustion chamber and the engine cooling system; and (3) reduction in the volume of the combustion zone which can cause a higher than design compression ratio in the engine. A knocking engine can also result from deposits forming and accumulating in the combustion chamber. A prolonged period of a knocking engine can result in stress fatigue and wear in engine components such as, for example, pistons, connecting rods bearings and cam rods.

The formation and accumulation of intake valve deposits can interfere with valve closing which eventually can result in valve burning. Such deposits can also interfere with valve motion and valve seating which tend to reduce the volumetric efficiency of the engine and limit the maximum design power. Deposits can also collect in the tubes and runners that are part of the exhaust gas recirculation (EGR) flow. The collection of these deposits can reduce the EGR flow. This will also result in a knocking engine and an increase in nitric oxide emissions.

Accordingly, it would be desirable to rapidly screen a plurality of sample candidate fuel compositions for deposit formation tendencies utilizing small amounts of each sample. In this manner, a high throughput preparation and screening of a vast number of diverse compositions can be achieved to identify which additives and/or compositions have reduced deposit formation tendencies.

SUMMARY OF THE INVENTION

A high throughput screening method for determining deposit formation tendencies of fuel compositions is provided herein. In accordance with one embodiment of the present invention, a high throughput method for screening fuel additive composition samples, under program control, is provided comprising the steps of (a) providing a plurality of different fuel additive composition samples, each sample comprising at least one fuel additive; (b) measuring the deposit formation of each sample to provide deposit formation data for each sample; and, (c) outputting the results of step (b).

In accordance with a second embodiment of the present invention, a high throughput method for screening fuel composition samples, under program control, is provided comprising the steps of (a) providing a plurality of different fuel composition samples, each sample comprising (i) a major amount of a fuel and (ii) a minor amount of at least one fuel additive; (b) measuring the deposit formation of each sample to provide deposit formation data for each sample; and, (c) outputting the results of step (b).

In a third embodiment of the present invention, a system for determining deposit formation tendencies of fuel additive composition samples is provided comprising:
  (a) a plurality of test receptacles, each receptacle containing a different fuel additive composition sample comprising at least one fuel additive;
  (b) receptacle moving means for individually positioning the test receptacles in a testing station for measurement of the deposit formation of the respective sample;
  (c) means for measuring the deposit formation of each respective sample in the testing station to obtain deposit formation data associated with the sample and for transferring the deposit formation data to a computer controller.

In a fourth embodiment of the present invention, a system for determining deposit formation tendencies of fuel composition samples is provided comprising:
  (a) a plurality of test receptacles, each receptacle containing a different fuel composition sample comprising (i) a major amount of a fuel and (ii) a minor amount of at least one fuel additive;
  (b) receptacle moving means for individually positioning the test receptacles in a testing station for measurement of the deposit formation of the respective sample;
  (c) means for measuring the deposit formation of each respective sample in the testing station to obtain deposit formation data associated with the sample and for transferring the deposit formation data to a computer controller.

The methods and systems of the present invention advantageously permit the screening of many different composition samples in an efficient manner to determine deposit formation tendencies of the samples, e.g., how fast deposits form, at what temperatures do deposits form and the weight of the deposits.

BRIEF DESCRIPTION OF THE DRAWINGS

Various embodiments are described below with reference to the drawings wherein.

DETAILED DESCRIPTION OF THE PREFERRED EMBODIMENT(S)

Figure 1:
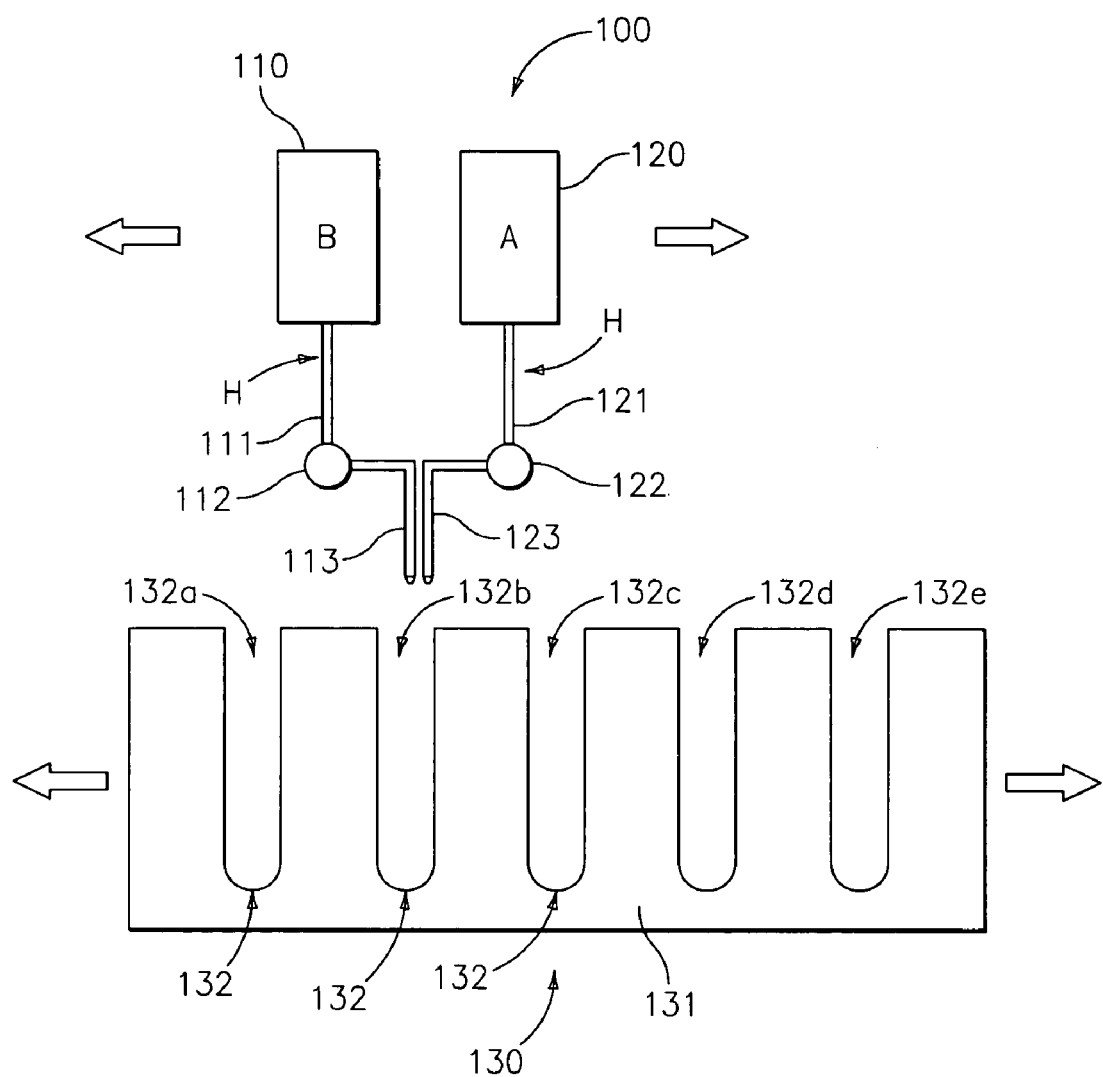
FIG. 1 is a schematic diagram of a system for preparing a plurality of different fuel compositions; and, FIG. 2 is a schematic diagram of a system for measuring deposit formation tendencies of a plurality of samples of fuel compositions.

The present invention is directed to a high throughput screening method for determining deposit formation tendencies of fuel additive compositions and fuel compositions containing such fuel additive compositions. The expression "high throughput" as used herein shall be understood to mean that a relatively large number of different fuel additive compositions or fuel compositions can be rapidly prepared and analyzed. In a first step of the screening method of the present invention, at least one fuel additive is introduced in a plurality of respective test receptacles so that each receptacle contains a different fuel additive composition having a different composition depending upon the percentage amounts and/or types of the additives combined in each receptacle.

Alternatively, varying quantities of at least fuel and at least one fuel additive are introduced in a plurality of respective test reservoirs so that each reservoir contains a different fuel composition having a different composition depending upon the percentage amounts and/or types of the additives combined with the fuel in each receptacle.

Data regarding the composition of each sample are stored in a data library. Adding the information related to the deposit formation data of each of the stored compositions substantially facilitates the selection of candidate compositions capable of successfully carrying out the deposit formation tests under the desired operating conditions or statutory requirements. Accordingly, storing this information in the combinatorial library not only allows for a rapid selection of multiple fuel compositions in response to new requirements for a given test, but also becomes another piece of information in addition to, for example, storage stability, of the cataloged compositions. This information may also allow for calculating necessary changes of the additives and fuels at the least cost. The procedure is advantageously accomplished under program control and automatically controlled by, for example, a microprocessor or other computer control device. The expression "program control" as used herein shall be understood to mean the equipment used herein in providing the plurality of fuel compositions is automated and controlled by a microprocessor or other computer control device.

The fuel additive compositions and fuel compositions for use in the high throughput screening method of this invention include at least one fuel additive. Such additives for use in the fuel additive and fuel compositions herein can be any presently known or later-discovered additive used in formulating fuel compositions. The fuel additives include, but are not limited to, detergents, cetane improvers, octane improvers, emission reducers, antioxidants, carrier fluids, metal deactivators, lead scavengers, rust inhibitors, bacteriostatic agents, corrosion inhibitors, antistatic additives, drag reducing agents, demulsifiers, dehazers, anti-icing additives, dispersants, combustion improvers and the like and mixtures thereof. A variety of the additives are known and commercially available. These additives, or their analogous compounds, can be employed for the preparation of the various fuel compositions.

Alternatively, the fuel additive(s) can further contain an inert stable oleophilic organic solvent to form an additive concentrate. These concentrates usually include at least from about 98 wt. % to about 10 wt. %, preferably from about 98 wt. % to about 25 wt. % and most preferably from about 97 wt. % to about 50 wt. % of an inert stable oleophilic organic solvent and from about 2 wt. % to about 90 wt. %, preferably from about 2 wt. % to about 75 wt. % and most preferably from about 3 wt. % to about 50 wt. %, of the foregoing additive(s). Useful inert stable oleophilic organic solvent can be solvents boiling in the range of about 150° F. to about 400° F. Examples of inert solvents include, but are not limited to, aliphatic hydrocarbon solvents, aromatic hydrocarbon solvents, e.g., benzene, toluene, xylene, etc., and the likle and mixtures thereof. Aliphatic alcohols containing 3 to about 8 carbon atoms, e.g., isopropanol, n-butanol and the like, in combination with the foregoing hydrocarbon solvents are also suitable for use with the fuel additive.

Examples of detergents include, but are not limited to, nitrogen-containing detergents such as, for example, aliphatic hydrocarbyl amines, hydrocarbyl-substituted poly (oxyalkylene) amines, hydrocarbyl-substituted succinimides, Mannich reaction products, nitro and amino aromatic esters of polyalkylphenoxyalkanols, polyalkylphenoxyaminoalkanes and post-treated derivatives of the foregoing nitrogen-containing compounds and the like and mixtures thereof.

Useful aliphatic hydrocarbyl-substituted amines which may be employed in the present invention are typically straight or branched chain hydrocarbyl-substituted amines having at least one basic nitrogen atom and wherein the hydrocarbyl group has a number average molecular weight of about 700 to about 3,000. Preferred aliphatic hydrocarbyl-substituted amines include polyisobutenyl and polyisobutyl monoamines and polyamines. The aliphatic hydrocarbyl amines employed in this invention are prepared by conventional procedures known in the art. Such aliphatic hydrocarbyl amines and their preparations are described in detail in U.S. Pat. Nos. 3,438,757; 3,565,804; 3,574,576; 3,848,056; 3,960,515; 4,832,702; and 6,203,584, the contents of each of which are incorporated by reference herein.

Useful hydrocarbyl-substituted poly(oxyalkylene) amines (also referred to as polyether amines) are generally hydrocarbyl-substituted poly(oxyalkylene) amines, e.g., hydrocarbyl poly(oxyalkylene) monoamines and polyamines wherein the hydrocarbyl group contains from 1 to about 30 carbon atoms, the number of oxyalkylene units range from about 5 to about 100, and the amine moiety is derived from ammonia, a primary alkyl or secondary dialkyl monoamine, or a polyamine having a terminal amino nitrogen atom. Preferably, the oxyalkylene moiety will be oxypropylene or oxybutylene or a mixture thereof. Such hydrocarbyl-substituted poly(oxyalkylene) amines are described, for example, in U.S. Pat. Nos. 5,112,364 and 6,217,624, the contents of which are incorporated by reference herein. A preferred type of hydrocarbyl-substituted poly(oxyalkylene) monoamine is an alkylphenyl poly(oxyalkylene)monoamine wherein the poly(oxyalkylene) moiety contains oxypropylene units or oxybutylene units or mixtures of oxypropylene and oxybutylene units.

An additional type of hydrocarbyl-substituted poly(oxyalkylene)amine are hydrocarbyl-substituted poly(oxyalkylene) aminocarbamates as disclosed, for example, in U.S. Pat. Nos. 4,160,648; 4,191,537; 4,197,409; 4,233,168; 4,236,020; 4,243,798; 4,270,930; 4,288,612 and 4,881,945, the contents of each of which are incorporated by reference herein. These hydrocarbyl poly(oxyalkylene)aminocarbamates contain at least one basic nitrogen atom and have an average molecular weight of about 500 to about 10,000, preferably about 500 to about 5,000, and more preferably about 1,000 to about 3,000. A preferred aminocarbamate is alkylphenyl poly(oxybutylene) aminocarbamate wherein the amine moiety is derived from ethylene diamine or diethylene triamine.

Useful hydrocarbyl-substituted succinimides are generally hydrocarbyl-substituted succinimides, e.g., polyalkyl and polyalkenyl succinimides wherein the polyalkyl or polyalkenyl group has an average molecular weight of about 500 to about 5,000, and preferably about 700 to about 3,000. The hydrocarbyl-substituted succinimides are typically prepared by reacting a hydrocarbyl-substituted succinic anhydride with an amine or polyamine having at least one reactive hydrogen bonded to an amine nitrogen atom. Preferred hydrocarbyl-substituted succinimides include polyisobutenyl and polyisobutanyl succinimides, and derivatives thereof. Examples of hydrocarbyl-substituted succinimides are described, for example, in U.S. Pat. Nos. 5,393,309; 5,588,973; 5,620,486; 5,916,825; 5,954,843; 5,993,497; and 6,114,542, and British Patent No. 1,486,144, the contents of each of which are incorporated by reference herein.

Useful Mannich reaction products are generally obtained from the Mannich condensation of a high molecular weight alkyl-substituted hydroxyaromatic compound, an amine containing at least one reactive hydrogen, and an aldehyde. The high molecular weight alkyl-substituted hydroxyaromatic compounds are preferably polyalkylphenols, e.g., polypropylphenol and polybutylphenol, wherein the polyalkyl group has an average molecular weight of about 600 to about 3,000. The amine reactant is typically a polyamine, such as alkylene polyamines, especially ethylene or polyethylene polyamines, for example, ethylene diamine, diethylene triamine, triethylene tetramine, and the like. The aldehyde reactant is generally an aliphatic aldehyde, such as formaldehyde, including paraformaldehyde and formalin, and acetaldehyde. A preferred Mannich reaction product is obtained by condensing a polyisobutylphenol with formaldehyde and diethylene triamine, wherein the polyisobutyl group has an average molecular weight of about 1,000. Examples of Mannich reaction products are described, for example, in U.S. Pat. Nos. 4,231,759 and 5,697,988, the contents of each of which are incorporated by reference herein.

Additional examples of the foregoing additives are described, for example, in U.S. Pat. Nos. 6,203,584; 6,616,776; 6,651,604 and 6,652,667, the contents of each of which are incorporated by reference herein.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol and the like and mixtures thereof.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; fatty acid amine salts; partial carboxylic acid ester of polyhydric alcohol; (short-chain) alkenyl succinic acids; partial esters thereof and nitrogen-containing derivatives thereof and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Pat. No. 4,729,769 and U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants may also be used. Preferably, the dispersants are polyalkylene succinimides derived from animation of polyalkylene succinic anhydrides with polyalkylene polyamine.

The fuel compositions for use in the high throughput screening method of this invention include a minor amount of at least one of the foregoing fuel additives together with a major amount of at least one fuel, e.g., an amount of greater than 50 wt. %, preferably greater than about 70 wt. %, more preferably from about 80 to about 99.9 wt. % and most preferably from about 90 to about 99.5 wt. %, based on the total weight of the composition. The fuel for use herein can be any presently known or later-discovered fuel used in formulating fuel compositions for any and all such applications and engines, e.g., a wide variety of two stroke and four stroke internal combustion engines such as port fuel injection spark ignition (PFISI) engines, direct injection spark ignition (DISI) engines, diesel, marine, natural gas and hydrogen fueled engines. Accordingly, fuels for use herein include, but are not limited to, motor fuels, e.g., gasoline or diesel which may also contain other components such as alcohols, ethers, or mixture thereof; kerosene; jet fuels; marine bunker fuel, natural gas, e.g., methane; home heating fuel and the like and mixture thereof.

For example, when the fuel is diesel, such fuel generally boils above about 212° F. The diesel fuel can comprise atmospheric distillate or vacuum distillate, or a blend in any proportion of straight run and thermally and/or catalytically cracked distillates. Preferred diesel fuels have a cetane number of at least about 40, preferably above about 45, and more preferably above about 50. The diesel fuel can have such cetane numbers prior to the addition of any cetane improver. The cetane number of the fuel can be raised by the addition of a cetane improver.

Also, when the fuel is gasoline, it can be derived from straight-chain naphtha, polymer gasoline, natural gasoline, catalytically cracked or thermally cracked hydrocarbons, catalytically reformed stocks, etc. It will be understood by one skilled in the art that gasoline fuels typically boil in the range of about 80° to about 450° F. and can contain, for example, straight chain or branched chain paraffins, cycloparaffins, olefins, aromatic hydrocarbons, and any mixture of these.

If desired, prior to dispensing the at least one fuel additive or the at least one fuel and the at least one fuel additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compounds libraries with increased probability for finding desirable compounds. For example, the compounds analyzed can be formulated into various fuel compositions, as decribed hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 10/699,510, filed on Oct. 31, 2003 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. It is to be understood that the present invention is not limited to this system and that other systems can be envisioned for providing the foregoing compositions in the plurality of respective test receptacles.

Generally, vessel 110 contains a supply of the foregoing fuels B. Vessel 120 contains a supply of additive A, which can be any of the foregoing additives useful for modifying the properties of the fuel. As one skilled in the art would readily appreciate, one or more of vessels 110 and vessels 120 can be used when dispensing more than one fuels and/or more than one additive, respectively. For example, in the case of screening fuel additive compositions, one or more vessels 120 can be used without operating vessel 110.

Tubular line 111 is a conduit for communicating the fuel B to nozzle portion 113, from which it can be dispensed into a selected test reservoir, as described below. The amount of fuel dispensed is determined by metering pump 112, which can be computer controlled.

Tubular line 121 is a conduit for communicating the fuel additive A to nozzle portion 123, from which it can be dispensed into a selected test reservoir, as described below. The amount of fuel additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that fuel B and additive A can be simultaneously dispensed in a test reservoir. Alternatively, fuel B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous fuel or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed fuel and additives. The recesses provide test reservoirs wherein each reservoir contains fuel additive compositions or fuel compositions of a different and predetermined composition, i.e., the percentage and/or type of fuel and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132a, 132b, 132c, 132d, 132e, are illustrated in FIG. 1, any number of reservoirs can be employed herein. For example the system can employ 20, 50, 100 or even more test receptacles and samples as required.

The individual reservoirs are adapted to hold relatively small amounts of fuel or additive samples. The sample size in each reservoir can generally be less than about 50 ml, preferably no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected fuel and additive(s), respectively. The apparatus of system 100 is moved such that dispensing nozzles 113 and 123 are positioned above and in alignment with recess 132a. A metered amount of fuel B and a metered amount of additive A are simultaneously dispensed into recess 132a. The dispensing nozzles 113 and 123 are thereafter repositioned to be in alignment with the next recess 132b and the metered amounts of additive A and/or fuel B are changed in accordance with a predetermined schedule of variation such that the fuel composition in recess 132b has a different percentage composition of fuel and/or additive than that in recess 132a. The pattern is repeated as the nozzles 113 and 123 are sequentially aligned with the successive recesses 132c, 132d, and 132e so that each recess has a predetermined composition of fuel.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, fuel B and additive(s) A can be combined prior to dispensing into the respective reservoirs. For example, a single dispensing nozzle having a mixing chamber can be used, wherein fuel B and additive(s) A are metered into the mixing chamber and then dispensed through the nozzle into the reservoir.

Figure 2:
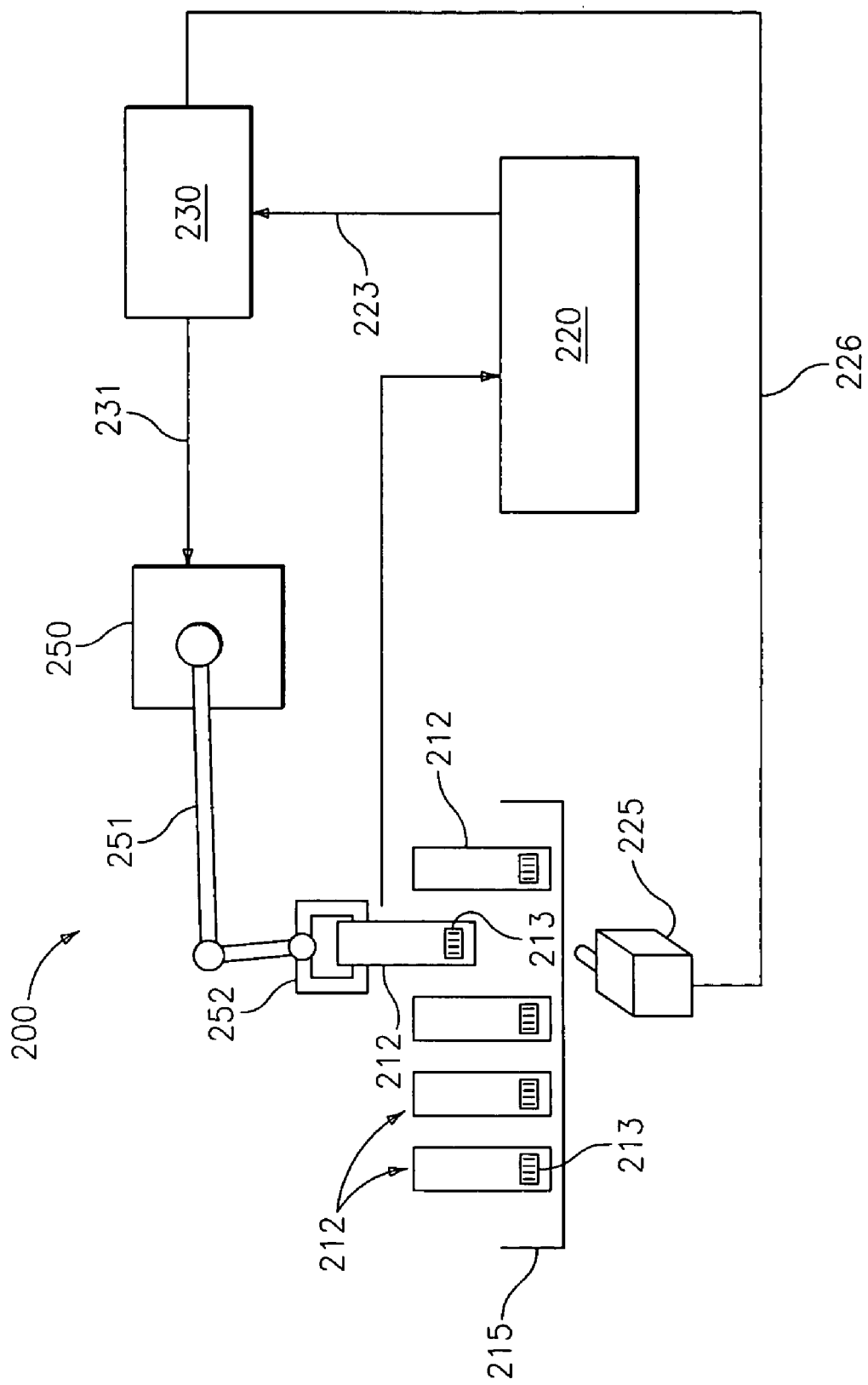

Once the plurality of receptacles have been provided containing fuel compositions, the plurality of fluid samples can then be analyzed for deposit forming tendencies. Referring now to FIG. 2, a system for sequentially analyzing a plurality of fluid samples for deposit formation is schematically illustrated. The samples can include fuel additive compositions containing at least one fuel additive or fuel compositions containing one or more fuels and one or more fuel additives, such as those described herein.

System 200 is schematically illustrated wherein an array of test receptacles 212 are mounted in a holder 215. The system 200 is adapted to accommodate any number of test receptacles 212 (and samples). Each sample is identifiable, for example, by the position of its test receptacle in an ordered array in holder 215, or more preferably by having an identifying mark associated with it. For example, each test receptacle 212 can include an identifying bar code 213 affixed to the outer surface thereof. A bar code reader 225 is positioned so as to be able to read the individual bar codes of the respective test receptacles 212 and to transmit a bar code data signal to a computer controller 230 via a data transmission line 226 to electronically identify the sample. The bar code reader 225 is preferably movable with respect to the holder 215 in response to a signal from computer controller 230 so as to be positionable in alignment with selected individual test receptacles 212.

A robotic assembly 250 includes a movable arm 251 with a grasping mechanism 252. The robotic assembly is adapted to grasp an individual test receptacle 212 in accordance with selection instructions from computer controller 230 and move the test receptacle to a position in testing station 220 so that the sample in the receptacle can be measured for deposit formation data. The computer controller 230 is operatively associated with controls to the robotic assembly via control signal transmission line 231 to selectively retrieve predetermined test receptacles for measurement and then replace them in their assigned respective positions in the holder 215.

Testing station 220 includes means for testing the samples for deposit formation. Deposit formation data results of the test are converted to an electrical or optical signal and transmitted via signal transmission line 223 to computer controller 230. Various means for deposit formation testing are known and generally include subjecting the sample to a deposit formation environment and measuring the deposit formation of the sample over a predetermined period of time.

For example, one deposit formation test method of the present invention utilizes thermal gravimetric analysis (TGA). In general, thermal gravimetric analysis is a technique to analyze a fuel additive for rate of thermal decomposition in order to determine whether the additive will increase fuel deposits, e.g., combustion chamber deposits. In this method, the sample containing at least one fuel additive is placed in a suitable vessel and heated to a predetermined temperature, e.g., from about 100° C. to about 450° C., by using any conventional heating source, under air flowing at a predetermined rate, e.g. about 30 to about 100 cubic centimeters per minute, and measuring its volatility after a predetermined period of time, e.g., from about 2 minutes to about 1 hour. Specifically, the sample is heated to a predetermined temperature, e.g., about 200° C., kept at this temperature for a predetermined period of time, e.g., about 30 minutes, and then further heated to a second predetermined temperature, e.g., about 300° C., where it is kept for an additional predetermined period of time, e.g., about 30 minutes. The weight of the sample, is recorded at the start, after the first heating period and after the final heating period. The difference in weights from the start to the first predetermined temperature and then from the first predetermined temperature to the second predetermined temperature is recorded and the percent loss, i.e., volatility, is calculated. (The final weight at the second predetermined temperature is also considered residue.) The weight loss percent of the fuel additive is then recorded.

In another test method for use herein a substrate, e.g., a metal substrate such as aluminum, is position in a testing station and heated to a predetermined temperature, e.g., a temperature ranging from about 80° C. to about 250° C. and preferably from about 125° C. to about 175° C. Preferably, the substrate is configured such that it is held on an incline, e.g., about 45 to 90°, to determine deposit formation. A sample of a fuel composition containing no fuel additive is then contacted with the substrate for a sufficient period of time for fuel deposits to form, e.g., a time period ranging from about 1 hour to about 48 hours. After the predetermined period of time, the substrate containing, if any, fuel deposits is weighed and this data is recorded. A sample of a fuel composition containing at least one additive, e.g., a detergent, is then contacted with the substrate containing deposits for a predetermined period of time e.g., a time period ranging from about 1 hour to about 48 hours. Next, the substrate is rinsed with a suitable solvent such as pentane and the substrate is then weighed. The effectiveness of the fuel composition containing the at least one additive for removing any pre-existing fuel deposits can then be determined by comparing the weight of the substrate containing deposits after being contacted with the fuel composition containing no fuel additive(s) to the weight of the substrate after being contacted with the fuel composition containing at least one fuel additive. The data is then recorded in a database.

If desired, an assigned value of deposit formation is programmed into the computer controller for "pass/fail" determination. Assigned pass/fail values can be selected based upon performance requirements for specific fuel applications and prospective operating environments. If the test sample fails by having an excessively high deposit formation value, the test sample can be electronically marked and future testing of fuel formulations having the same composition as the sample can be eliminated from further testing for other performance characteristics. By not retesting failed samples the system can be made to operate more efficiently, energy and time being spent only on samples which prospectively meet the desired product specifications.

If desired, the results of the methods of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

Deposit formation data regarding each of the compositions described herein can be stored in a relational database to provide a combinatorial fuel composition library. Alternatively, the system may be electrically connected to a signal data collector comprising a computer microprocessor for system operation and control to collect the data from the various tests over an extended period of time to compile the combinatorial fuel composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the fuel compositions to the analytical deposit formation data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of each of the additives and compositions described herein and correlate that information with the information obtained from the deposit formation measurements can be used. This type of software is well known to those of skill in the art.

While the above description contains many specifics, these specifics should not be construed as limitations of the invention, but merely as exemplifications of preferred embodiments thereof. For example, deposit formation tendency tests other than those described herein can be used to provide deposit formation data for the plurality of different samples tested. Those skilled in the art will envision many other embodiments within the scope and spirit of the invention as defined by the claims appended hereto.

What is claimed is:

1. A high throughput method for screening fuel additive composition samples, under program control, comprising:
   (a) conducting molecular modeling of at least one fuel additive to formulate a leading candidate fuel additive composition sample for testing;
   (b) containing a plurality of the leading candidate fuel additive composition samples in a plurality of test receptacles, each sample comprising at least one fuel additive, wherein the plurality of leading candidate fuel additive composition samples is at least 20;
   (c) measuring the deposit formation of each sample to provide deposit formation data results for each sample, wherein the step of measuring the deposit formation of each sample comprises heating the sample to a first predetermined temperature and determining the weight loss of the sample after a first predetermined period of time; and,
   (d) outputting the results of step (c), wherein the results of step (c) for each sample are transmitted to a computer, wherein the computer compares the results with a predetermined value delimiting a failure or passing of the results, and the computer identifies failed samples to preclude further testing of the failed samples.

2. The method of claim 1, wherein the at least one fuel additive is selected from the group consisting of detergents, cetane improvers, octane improvers, emission reducers, antioxidants, carrier fluids, metal deactivators, lead scavengers, rust inhibitors, bacteriostatic agents, corrosion inhibitors, antistatic additives, drag reducing agents, demulsifiers, dehazers, anti-icing additives, dispersants, combustion improvers and mixtures thereof.

3. The method of claim 1, wherein the at least one fuel additive is a detergent.

4. The method of claim 2, wherein the detergent is selected from the group consisting of aliphatic hydrocarbyl amines, hydrocarbyl-substituted poly(oxyalkylene) amines, hydrocarbyl-substituted succinimides, Mannich reaction products, nitro and amino aromatic esters of polyalkylphenoxyalkanols, polyalkylphenoxyaminoalkanes and mixtures thereof.

5. The method of claim 1, wherein the predetermined temperature is from about 100° C. to about 450° C. and the predetermined period of time is from about 2 minutes to about 1 hour.

6. The method of claim 1, wherein the weight loss of the sample is determined by thermal gravimetric analysis.

7. The method of claim 1, wherein the step of heating the sample is conducted in the presence of air.

8. The method of claim 1, wherein the step of measuring the deposit formation of each sample comprises heating the sample to the first predetermined temperature and determining the weight loss of the sample after the first predetermined period of time and then heating the sample to a second predetermined temperature and determining the weight loss of the sample after a second predetermined period of time.

9. The method of claim 8, wherein the second predetermined temperature is higher than the first predetermined temperature.

10. The method of claim 1, wherein the fuel additive composition further comprises an inert solvent.

11. The method of claim 1, wherein a robotic assembly selectively retrieves the samples from an array of samples and individually positions the samples in a testing station for determination of the deposit formation.

12. The method of claim 11, wherein said robotic assembly is controlled by a computer.

13. The method of claim 1, wherein the step of outputting comprises storing the results of step (d) on a data carrier.

14. The method of claim 1, further comprising the step of using the results of step (d) as a basis for obtaining a result of further calculations.

15. The method of claim 1, further comprising the step of transmitting the results of step (c) to a data carrier at a remote location.

16. The method of claim 1, wherein the fuel additive composition samples each contain less than about 50 ml.

17. The method of claim 1, wherein the fuel additive composition samples each contain less than about 20 ml.

18. The method of claim 1, wherein the plurality of leading candidate fuel additive composition samples is at least 50.

19. The method of claim 1, wherein the plurality of leading candidate fuel additive composition samples is 100 or more.

* * * * *